United States Patent [19]

Kiener

[11] Patent Number: 5,352,592
[45] Date of Patent: Oct. 4, 1994

[54] MICROBIOLOGICAL PROCESS FOR THE PRODUCTION OF 5-HYDROXYPYRAZINECARBOXYLIC ACID

[75] Inventor: Andreas Kiener, Visp, Switzerland

[73] Assignee: Lonza Ltd., Gampel/Valais, Switzerland

[21] Appl. No.: 84,462

[22] Filed: Jul. 1, 1993

[30] Foreign Application Priority Data

Jul. 8, 1992 [CH] Switzerland .................. 2150/92

[51] Int. Cl.$^5$ .................. C12P 17/12; C12P 7/42; C12N 1/20
[52] U.S. Cl. .................. 435/122; 435/146; 435/252.2
[58] Field of Search .................. 435/122, 252.2, 146

[56] References Cited

U.S. PATENT DOCUMENTS

| | | | |
|---|---|---|---|
| 4,800,162 | 1/1989 | Matson | 435/280 |
| 5,238,829 | 8/1993 | Keiner | 435/122 |

FOREIGN PATENT DOCUMENTS

| | | | |
|---|---|---|---|
| 0519512 | 6/1992 | European Pat. Off. | C12P 17/12 |
| 0529653 | 8/1992 | European Pat. Off. | C12P 17/10 |

OTHER PUBLICATIONS

Patent Abstracts of Japan, Unexamined Applications, C Field, vol. 12, No. 148, (No. 62-263164).
Kobayashi et al., J. of Antibiotics, XLIII (10):136-1320, Oct. 1990.
Weiner et al., J. Pharmacol. Exp. Ther., 180(2), (1972), pp. 411-434.
M. Bobek, J. Heterocyclic Chem. 28, (1991), p. 1131.

*Primary Examiner*—Irene Marx
*Assistant Examiner*—Maria Luisa Osoteo
*Attorney, Agent, or Firm*—Fisher, Christen & Sabol

[57] ABSTRACT

A microbiological process for the production of 5-hydroxypyrazinecarboxylic acid and/or its salts with microorganisms of the strain Agrobacterium sp. DSM 6336 or descendants thereof or mutants thereof, utilizing 3-cyanopyridine.

7 Claims, No Drawings

MICROBIOLOGICAL PROCESS FOR THE PRODUCTION OF 5-HYDROXYPYRAZINECARBOXYLIC ACID

BACKGROUND OF THE INVENTION

1. Field of the Invention

The invention relates to a new process for the production of 5-hydroxypyrazinecarboxylic acid and/or its salts with microorganisms of the strain Agrobacterium sp. DSM 6336 or descendants thereof or mutants, such descendants and mutants having the capability to utilize 3-cyanopyridine as their sole carbon, nitrogen and energy source and which have the capability to convert 2-cyanopyrazine into 5-hydroxypyrazine carboxylic acid.

In the following document, the term 5-hydroxypyrazinecarboxylic acid also means its salts, for example, its alkali salts or ammonium salts.

2. Background Art

It is known that 5-hydroxypyrazinecarboxylic acid in the metabolism of dogs and humans is formed from pyrazinamide by pyrazinecarboxylic acid [J. Pharmacol. Exp. Ther., 180(2), (1972), pp. 411–434].

A microbiological process for the production of 5-hydroxy-pyrazinecarboxylic acid is known from European Published Patent Application No. 0519512. In this process 5-hydroxypyrazinecarboxylic acid is produced starting from pyrazinecarboxylic acid by microorganisms utilizing nicotinic acid.

A great drawback of this process is that the feedstock, the pyrazinecarboxylic acid, is difficult to obtain.

BROAD DESCRIPTION OF THE INVENTION

The main objective of the invention was to make available both a simple and economical as well as an ecological process for the production of 5-hydroxypyrazinecarboxylic acid. Other objectives and advantages of the invention are set out herein or are obvious or apparent herefrom to one skilled in the art.

The objectives and advantages of the invention are achieved by the process of the invention.

The invention involves a microbiological process for the production of 5-hydroxypyrazinecarboxylic acid and/or its salts. The process involves converting 2-cyanopyrazine as the substrate with a microorganism, which grows with 3-cyanopyridine as the sole carbon, nitrogen and energy source, into 5-hydroxypyrazinecarboxylic acid and/or its salts and accumulating the latter in the medium.

The reaction (conversion) is performed with the microorganism of the strain Agrobacterium sp. DSM 6336 or a descendant thereof or a mutant thereof. Preferably the effective enzymes of the microorganism are induced with 3-cyanopyridine. Preferably the reaction (conversion) takes place under substrate addition all at once or continuously, so that the substrate concentration does not exceed 20 percent by weight. Preferably the reaction (conversion) is performed at a pH of 4 to 10 and a temperature of 10° to 60° C.

5-Hydroxypyrazinecarboxylic acid can be used, for example, as an intermediate product for the production of pharmaceutical agents, such as, for the production of pyrazine-nucleoside analogs with cytostatic effect [M. Dobek, J. Heterocyclic Chem., 28, (1991), p. 1131].

DETAILED DESCRIPTION OF THE INVENTION

According to the invention, 2-cyanopyrazine as the substrate is converted with the microorganism of the strain Agrobacterium sp. DSM 6336 or a descendant thereof or a mutant thereof, which grows with 3-cyanopyridine as the sole carbon, nitrogen and energy source, into 5-hydroxypyrazinecarboxylic acid (and/or a salt thereof) and the latter is accumulated in the medium. Examples of the salts of 5-hydroxypyrazinecarboxylic acid are the ammonium salt thereof and the alkali (metal) salts thereof, for example, the sodium, potassium and lithium salts thereof.

The phrase the microorganism which grows with 3-cyanopyridine as sole carbon, nitrogen and energy source," comprises both mixtures of the microorganisms and pure isolates of the microorganisms, which can be used under sterile or nonsterile fermentation conditions. Such mutants and descendants are those which have the same biological capability as the strain Agrobacterium sp. DSM 6336 to effect such conversion—they also grow with 3-cyanopyridine as the sole carbon, nitrogen and energy source. The strain Agrobacterium sp. (DSM 6336) was deposited with the Deutsche Sammlung für Mikroorganismen und Zellkulturen GmbH [German Collection for Microorganisms and Cell Cultures GmbH] (DSM), Mascheroderweg 1b, D-3300 Braunschweig, Germany, on Feb. 7, 1991, with the designation DSM 6336.

The following is the scientific (taxonomic) description of the strain Agrobacterium sp. (DSM 6336):

| Properties of the strain: | | | |
|---|---|---|---|
| cell shape | rods | ADH | − |
| width, micron | 0.6–0.8 | | |
| length, micron | 1.5–3.0 | ADC | − |
| mobility | + | ONPG | − |
| gram reaction | − | VP | − |
| lysis by 3% KOH | + | | |
| aminopeptidase (Cerni) | + | indole | − |
| spores | − | NO$_2$ from NO$_3$ | + |
| oxidase | + | denitrification | + |
| catalase | + | phenylalanine desaminase k.W. | |
| growth | | lecithinase | − |
| anaerobic | − | | |
| 37°/41° C. | ± | urease | + |
| pH 5.6 | − | | |
| MacConkey broth | + | Simmons citrate | − |
| SS agar | − | | |
| Cetrimide agar | − | malonate | − |
| 2% NaCl | + | | |
| | | ketolactose | − |
| pigments | − | | |
| nondiffusing | − | hydrolysis of | |
| diffusing | − | starch | − |
| fluorescent | − | gelatin | − |
| pyocyanine | − | casein | − |
| | | DNA | − |
| acid from (OF test) | | Tween 80 | |
| aerobic glucose | − | aesculin | + |
| anaerobic glucose | − | | |
| gas from glucose | − | alkalization of litmus milk | − |
| acid from (ASA) | | growth substance requirement | − |
| glucose | + | | |
| fructose | + | use of substrate | |
| xylose | + | acetate | + |
| m-erythritol | + | adipate | − |
| melezitose | − | caprate | − |
| arabinose | + | citrate | − |
| saccharose | − | glycolate | − |

-continued

Properties of the strain:

| | | | |
|---|---|---|---|
| cellobiose | + | lactate | + |
| trehalose | − | levulinate | − |
| rhamnose | + | malate | + |
| dulcitol | − | malonate | − |
| sorbitol | + | phenylacetate | − |
| glycerol | + | suberate | − |
| L-arabinose | + | | |
| fructose | + | | |
| glucose | + | | |
| mannose | + | | |
| maltose | + | | |
| xylose | + | | |
| saccharose | + | | |
| sorbose | − | | |
| mannitol | + | | |
| 2-ketogluconate | − | | |
| N-acetylglucosamine | + | | |
| L-serine | − | | |
| hydroxybutyrate | − | | |
| L-lysine | + | | |
| L-ornithine | + | | |

Usually the microorganisms are cultivated (cultured) before the actual reaction (conversion) and their effective enzymes are induced. Preferably, the cultivation (culture) and the induction take place with 3-cyanopyridine as the sole carbon, nitrogen and energy source.

Before the addition of the substrate (2-cyanopyrazine), the microorganisms then can either be harvested by usual separating processes and resuspended in a fresh medium or the substrate (2-cyanopyrazine) can be added directly to the microorganisms in the initial growth medium.

The strain for the actual process the cell suspension suitably is then adjusted to an optical density, at 650 nm, of 1 to 100, preferably of 10 to 40.

As the media, those usual among experts (those skilled in the art) can be used both for the cultivation and for the actual reaction.

The substrate (2-cyanopyrazine) can be added all at once or continuously. Suitably, the substrate addition takes place so that the substrate concentration does not exceed 20 percent by weight, preferably 8 percent by weight. Usually the reaction of 2-cyanopyrazine to 5-hydroxypyrazinecarboxylic acid takes place with dormant cells. Suitably the reaction takes place at a pH of 4 to 10, preferably at a pH of 6 to 8. The temperature suitably is between 10° and 60° C., preferably between 15° and 45° C.

After a usual reaction time of 4 to 100 hours, the product can be precipitated by acidification of the cell-free solution and obtained by working-up methods usual to one skilled in the art.

EXAMPLE

Agrobacterium sp. DSM 6336 was cultivated in a mineral salt medium (Table 1) under an addition of 0.1 percent (w/v) 3-cyanopyridine at a temperature of 30° C. in a 300 ml Erlenmeyer flask. After 36 hours growth, the cells were centrifuged off and washed in the same medium without 3-cyanopyridine. Then 25 ml of the cell suspension with an optical density of 10 at 650 nm was mixed with 297 mg (2.83 mmol) of 2-cyanopyrazine and incubated during 16 hours on a shaker. After this incubation time no more initial material was able to be detected in the UV spectrum. Then the cells were centrifuged off and the supernatant concentrated five times on a rotary evaporator and acidified with concentrated HCl to pH 2.0. The precipitated 5-hydroxypyrazinecarboxylic acid was filtered off and dried. Altogether 307 mg (2.21 mmol) of product was isolated, corresponding to a yield of 78 percent. No impurities were detected in the $^1$H-NMR spectrum (D$_2$O).

TABLE 1

A + N medium

| Composition | Concentration (mg/l) |
|---|---|
| $(NH_4)_2SO_4$ | 2000 |
| $Na_2HPO_4$ | 2000 |
| $KH_2PO_4$ | 1000 |
| NaCl | 3000 |
| $MgCl_2.6H_2O$ | 400 |
| $CaCl_2.2H_2O$ | 14.5 |
| $FeCl_2.6H_2O$ | 0.8 |
| pyridoxal hydrochloride | $10 \cdot 10^{-3}$ |
| riboflavin | $5 \cdot 10^{-3}$ |
| nicotinic acid amide | $5 \cdot 10^{-3}$ |
| thiamin hydrochloride | $2 \cdot 10^{-3}$ |
| biotin | $2 \cdot 10^{-3}$ |
| pantothenic acid | $5 \cdot 10^{-3}$ |
| p-aminobenzoate | $5 \cdot 10^{-3}$ |
| folic acid | $2 \cdot 10^{-3}$ |
| vitamin B12 | $5 \cdot 10^{-3}$ |
| $ZnSO_4.7H_2O$ | $100 \cdot 10^{-3}$ |
| $MnCl_2.4H_2O$ | $90 \cdot 10^{-3}$ |
| $H_3BO_3$ | $300 \cdot 10^{-3}$ |
| $CoCl_2.6H_2O$ | $200 \cdot 10^{-3}$ |
| $CuCl_2.2H_2O$ | $10 \cdot 10^{-3}$ |
| $NiCl_2.6H_2O$ | $20 \cdot 10^{-3}$ |
| $Na_2MoO_4.2H_2O$ | $30 \cdot 10^{-3}$ |
| $EDTANa_2.2H_2O$ | 5.0 |
| $FeSO_4.7H_2O$ | 2.0 |

(pH of the solution was adjusted to 7.0)

What is claimed is:

1. A process for the production of 5-hydroxypyrazinecarboxylic acid or a salt thereof, comprising converting the substrate 2-cyanopyrazine to 5-hydroxypyrazinecarboxylic acid or a salt thereof with Agrobacterium sp. DSM 6336 or mutants thereof capable of said conversion and wherein said mutant utilizes 3-cyanopyridine as its sole carbon, nitrogen and energy source, and isolating the 5-hydroxypyrazinecarboxylic acid or salt thereof from the medium.

2. A process according to claim 1, wherein the conversion takes place with a single or continuous substrate addition, so that the substrate concentration does not exceed 20 percent by weight.

3. A process according to claim 2, wherein the conversion is performed at a pH of 4 to 10 and a temperature of 10° to 60° C.

4. A process according to claim 1, wherein the substrate concentration does not exceed 8 percent by weight.

5. A process according to claim 1, wherein the conversion is performed at a pH of 4 to 10 and a temperature of 10° to 60° C.

6. A process according to claim 5, wherein the pH is 6 to 8 and the temperature is 15° to 45° C.

7. A process according to claim 1, wherein the salt of the 5-hydroxypyrazinecarboxylic acid is an alkali salt.

* * * * *